US010973550B2

(12) United States Patent
Wurapa

(10) Patent No.: US 10,973,550 B2
(45) Date of Patent: Apr. 13, 2021

(54) MONOPLANAR HINGED ADJUSTABLE EXTERNAL FIXATOR FOR BONE FIXATION AND DISTRACTION

(71) Applicant: Raymond K. Wurapa, Blacklick, OH (US)

(72) Inventor: Raymond K. Wurapa, Blacklick, OH (US)

(73) Assignee: Raymond K. Wurapa, Blacklick, OH (US)

( * ) Notice: Subject to any disclaimer, the term of this patent is extended or adjusted under 35 U.S.C. 154(b) by 0 days.

(21) Appl. No.: 16/401,098

(22) Filed: May 1, 2019

(65) Prior Publication Data
US 2019/0336172 A1 Nov. 7, 2019

Related U.S. Application Data

(60) Provisional application No. 62/665,466, filed on May 1, 2018.

(51) Int. Cl.
*A61B 17/64* (2006.01)
*A61B 17/66* (2006.01)

(52) U.S. Cl.
CPC ...... *A61B 17/6425* (2013.01); *A61B 17/6416* (2013.01); *A61B 17/66* (2013.01)

(58) Field of Classification Search
CPC . A61B 17/6425; A61B 17/6416; A61B 17/66; A61B 17/645; A61B 17/6458; A61B 17/6466; A61B 17/62; A61B 17/6433; A61B 17/64; B25B 1/14; B25B 1/20; B25B 5/085; B25B 5/082; B25B 5/101; Y10T 24/4441; Y10T 244/4513

USPC ...................................................... 606/64–29
See application file for complete search history.

(56) References Cited

U.S. PATENT DOCUMENTS

| | | | | | |
|---|---|---|---|---|---|
| 4,628,919 A | * | 12/1986 | Clyburn | ............. | A61B 17/6491 606/55 |
| 5,152,280 A | * | 10/1992 | Danieli | ............. | A61B 17/6458 606/54 |
| 5,167,661 A | * | 12/1992 | Wagenknecht | ...... | A61B 17/645 403/165 |
| 5,304,177 A | * | 4/1994 | Pennig | ............... | A61B 17/6416 403/374.3 |
| 5,941,877 A | * | 8/1999 | Viegas | ............... | A61B 17/6425 606/54 |
| 5,976,125 A | | 11/1999 | Graham | | |
| 6,162,223 A | * | 12/2000 | Orsak | ................ | A61B 17/6425 606/59 |
| 7,507,240 B2 | * | 3/2009 | Olsen | ................ | A61B 17/6416 606/57 |

(Continued)

OTHER PUBLICATIONS

Mikai Complete System; 2016 Mikai S.p.A., www.mikai.us/medical-surgery-devices.

*Primary Examiner* — Pedro Philogene
(74) *Attorney, Agent, or Firm* — McNees Wallace & Nurick LLC

(57) ABSTRACT

An adjustable dynamic distraction mechanism connects proximal and distal components of a fixator system to enable adjustment of the distraction between proximal and distal bones of a joint and fixation thereof. The device is dynamic in that once fixation of distraction is set, the distal portion of the anatomy may be permitted to move essentially freely to flex and extend by rotation at the natural axis of the joint.

20 Claims, 3 Drawing Sheets

(56) References Cited

U.S. PATENT DOCUMENTS 9,750,538 B2\* 9/2017 Soffiatti ............. A61B 17/6458
9,867,637 B2\* 1/2018 Sanders ............. A61B 17/6416

\* cited by examiner

MONOPLANAR HINGED ADJUSTABLE EXTERNAL FIXATOR FOR BONE FIXATION AND DISTRACTION

RELATED APPLICATIONS AND PRIORITY CLAIM

This application claims the benefit under 35 U.S.C. § 119(e) to U.S. Provisional Application Ser. No. 62/665,466 filed May 1, 2018, the entirety of which is incorporated herein by reference.

FIELD

The disclosure relates generally to a medical device for fixation and distraction of joint dislocations and fractures. In some particular embodiments, the medical device is useful for dislocations, fractures and comminuted fractures of the proximal interphalangeal joint.

BACKGROUND

Injuries to joints present a variety of challenges, including achieving controlled distraction and fixation and preserving motion of the joint during healing. For example, joints of the digits of a human hand are commonly injured during day to day activities. Existing solutions for fixing the bones, in particular for the commonly injured bones of the proximal interphalangeal joint, are bulky, imprecise with respect to distraction, and do not provide for natural flexion and extension. There exists a need for distraction and fixation solutions that provide a hinged design based on the native joint axis to allow more anatomic mobilization of an affected joint and with minimal bulk to improve patient tolerance.

SUMMARY

In accordance with the various embodiments a medical device for fixation and distraction of a joint, for example a phalangeal joint, is provided to address an injury to the joint such as a dislocation or fracture. The medical device is in the form of a fixator/distractor device that is monoplanar and includes an adjustable dynamic distraction mechanism for connecting proximal and distal components of a fixator system to bone.

In an embodiment, provided is a joint distraction device that includes at least two bone engagement modules that each compromise at least one assembly comprising a bone pin and a clamp, each clamp being connectable to the bone pin and a rod. The device further includes two elongate rigid rods that are connectable at respective ends to one another to form a rod assembly that can be extended to form a substantially linear rigid assembly having a shared axis, the rod assembly including a constrained pivot axis at the joinder of the rod ends, the axis being perpendicular to the rod shared axis, wherein one or more of the rods may be moved of the shared axis by rotation of its end around the rod assembly pivot axis. At least one bone engagement module is connectable to one rod to form a stabilization portion and at least one bone engagement module is connectable to the other rod to form a distraction portion. Translation of one or the other module along the connected rod axis provides for relative displacement between the two bone engagement modules. The device is adapted for fixation to respective proximal and distal bones at a joint axis between the bones, and wherein upon engagement therewith via insertion of the pins into the respective bones, a displacement of the bone engagement model fixed to the distal bone either distracts or compresses the joint between the bones, and wherein upon locking of the position of the bone engagement model fixed to the distal bone, the device fixates the joint and the pivot axis of the rod assembly permits constrained motion of the distal bone around the pivot axis. In some embodiments a bone engagement module includes one pin and clamp assembly. In other embodiments, such as exemplified herein, a bone engagement module includes two pin and clamp assemblies.

In an exemplary embodiment, the fixator/distractor device includes:
 a plurality of pins for insertion into bones adjacent an anatomical joint,
 a planar assembly comprising
 a plurality of clamps engageable with one or more of each of the plurality of pins;
 at least two rods, each of which is adapted with an engagement feature at one or more ends, each rod having an engagement feature that is complimentary with an engagement feature on at least one other rod, the at least two rods being joinable to form a releasable and adjustable pivot axis that is constrained to rotation around an axis that is transverse to the axis of the joined rods, the rods being constrained to move relative to one another only around the pivot axis, and
 one or more actuators attachable to at least one rod and engageable therewith for contacting at least one clamp, the actuator and the at least one rod each comprising commentary translation features to direct translation of one or more clamps along an axis defined by the rod,
 wherein each of the rods is engageable with one or more of the plurality pins via one or more clamps, and at least a first pin is affixed to at least one rod via a clamp that is engaged with an actuator, the first pin being movable relative to at least a second pin that is affixed to a rod on the opposite side of the pivot joint, whereby actuation of the at least one actuator moves one of the first and second pins towards or away from the other.

In some embodiments, the fixator/distractor device includes four pins, four clamps, two rods and at least one actuator, wherein two pins are fixedly clamped to a first rod, and two pins are releasably clamped to a second rod that is joined with the first rod to provide a pivot axis, the pins clamped to the second rod being in communication with at least one actuator to direct translation of the clamped pins along the axis of the second bar so as to move the respective clamp-pin assemblies closer to or farther from one another.

In some embodiments, one or more of the pins, clamps and rods is radiolucent.

In some embodiments, the first rod has a generally smooth surface and wherein the second rod comprises a thread along at least a portion of its surface, and wherein the at least one actuator is a nut with a through hole that receives the threaded second rod and includes on the surface of the through hole a complimentary thread to engage with the threaded second rod.

In another exemplary embodiment, the fixator/distractor device includes:
 (i) a plurality of bone pins (wires, screws and the like as known in the art) for insertion into bones adjacent a joint;
 (ii) a plurality of clamps, each clamp connectable to a bone pin;
 (ii) a rod assembly comprised of a distraction rod and a stabilization rod, each engageable with one or more of the plurality pins via the plurality of clamps, wherein the rods are joinable to form a releasable and adjustable pivot axis, the rods of the assembly each adapted for alignment along a digit. In accordance with the various embodiments, the rods are rigid and formed of a material that resists bending and distortion when forces associated with joint motion are applied to the device.

The plurality of bone pins and plurality of clamps are assembled in the fixator/distractor device to form two modules, each of which module includes at least one clamp engaged with a bone pin, the modules including a distraction module which, in use, is engaged on the distal bone of the joint and is connectable to the rod assembly frame on the distraction rod, and a stabilization module which, in use, is engaged on the proximal bone of the joint and is connectable to the rod assembly frame on the stabilization rod.

The device is adjustable to enable controlled and lockable distraction between the proximal and distal bones of the joint by movement of the distal bone away from the joint via displacement of the distraction module either proximally or distally along the distraction rod. The device is dynamic in that once fixation of distraction is set, the distal portion of the anatomy may be permitted to move essentially freely to flex and extend by rotation at the natural axis of the joint. In some embodiments, the device is adapted to be lockable to prevent dynamic flexion and extension of the anatomy.

In some embodiments the fixator/distractor device includes compression/distraction actuators that in some particular embodiments comprise nuts that are lockable adjacent one or both sides of the distraction module to prevent translation of the distraction module along an axis defined by the distraction rod of the rod assembly.

Also provided is a method for achieving joint fixation and distraction with or without anatomical motion at or near the native joint axis.

Other features and advantages of the present invention will be apparent from the following more detailed description, taken in conjunction with the accompanying drawings which illustrate, by way of example, the principles of the invention.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description.

Figure 1:
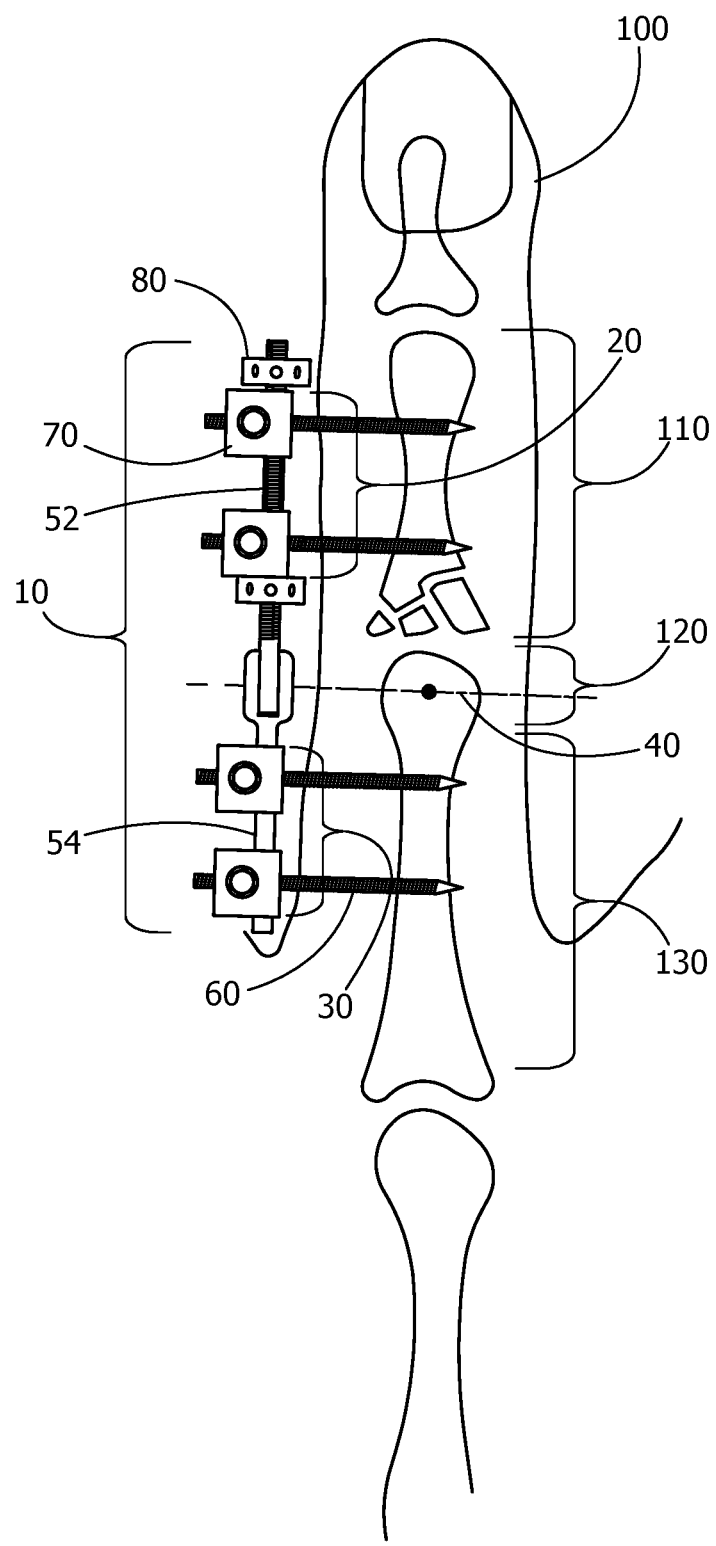
FIG. 1 shows a top planar view of a digit of a human hand with an embodiment of the medical fixation device according to the disclosure affixed to provide stable fixation and distraction of the bones particularly in the context of a comminuted fracture of the proximal interphalangeal joint.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

| Reference Numerals: | |
| --- | --- |
| 10 | fixator/distracter device |
| 20 | distraction module |
| 30 | stabilization module |
| 40 | proximal phalanx head |
| 45 | pivot axis |
| 50 | rod assembly |
| 52 | distraction rod |
| 54 | stabilization rod |
| 55 | threads |
| 56 | pivot head |
| 58 | pivot clevis |
| 60 | bone pin |
| 70 | clamp |
| 72 | rod retainer |
| 74 | flexion relief |
| 76 | locking assembly |
| 80 | distraction locking nut |
| 82 | driver receivers |
| 100 | human digit |
| 110 | distal phalanx |
| 120 | PIP joint |
| 130 | proximal phalanx |

DESCRIPTION

The general inventive concepts will now be described with occasional reference to the exemplary embodiments. Unless otherwise defined, all technical and scientific terms used herein have the same meaning as commonly understood by one of ordinary skill in the art encompassing the general inventive concepts. The terminology set forth in this description is for describing particular embodiments only and is not intended to be limiting of the general inventive concepts.

In accordance with the various embodiments and as described herein and depicted in the drawings, the invention is directed in various aspects to a medical device for fixation and distraction of a joint, for example a phalangeal joint, to address an injury to the joint such as a dislocation or fracture. It will be appreciated that the medical device may be exemplified in the context of a phalangeal joint, but its use is not limited, and the device may be utilized to stabilize and distract other joints wherein the scale and the number of pin and clamp components may be varied to accommodate the particulars of the target joint anatomy.

Generally, the medical device is a monoplanar adjustable dynamic distraction mechanism for connecting proximal and distal components of fixator system to bone, the proximal and distal components including a plurality of bone pins, and the distraction mechanism including clamps that are connected with the bone pins and with rods that form a frame for the monoplanar distraction mechanism. The device is adjustable insofar as it includes components that enable adjustment of the distraction between the proximal and distal bones of the joint by movement of the distal bone away from the joint. The device is dynamic in that once fixation of distraction is set, the distal portion of the anatomy may be permitted to move essentially freely to flex and extend by rotation at the natural axis of the joint. In some embodiments, the device is adapted to be lockable to prevent dynamic flexion and extension of the anatomy. Thus, the device may be employed in one or the other of a dynamic active mode that permits one or both of natural flexion and extension, and in a static locked mode that limits or wholly restricts one or both of natural flexion and extension. In some embodiments, restriction of motion may be complete using stops or other locks on the pivot axis. And in some embodiments motion may be partially restricted with limits on the range of flexion/extension.

In some embodiments, the device may be formed of radiopaque material. In certain preferred embodiments, at least some of the components of the device are radiolucent to enable visualization of the bones under radiography. In some such embodiments, the pins, rods and wires may be formed of metal, for example but not limited to stainless steel, titanium and other suitable medical grade metals, and the frame that comprises rods and clamps is formed primarily of radiolucent materials that may, in some embodiments, include tantalum or other type radiopaque markers to register position of the device when applied to the anatomy. In accordance with the various embodiments, the rods and the pins are generally rigid and formed of a material that resists bending and distortion when forces associated with joint motion are applied to the device.

Though not intending to be limiting, it is contemplated that the device is applied to only one side of a joint to limit bulk and allow motion of the digit. The device may be used specifically for reduction and distraction of small joint fracture or dislocation injuries, by inserting two stainless steel wires or pins each to proximal and distal bones, the pins connected to an adjustable radiolucent frame formed of a rod assembly, wherein manipulation and distraction of the bones is aided by fluoroscopic imaging prior to locking fixation of distraction of the distal bone.

Referring now to the drawings, as shown in FIG. 1, the fixator/distractor device 10 includes a plurality of bone pins 60 (wires, screws and the like as known in the art) for insertion into bones adjacent a joint, a rod assembly 50 comprised of a distraction rod 52 and a stabilization rod 54, each engageable with one or more of the plurality pins 60 via a plurality of clamps 70, the rods 52, 54 being joinable via rod ends at a releasable and adjustable pivot axis 45 adapted for alignment along the digit 100 adjacent the joint (the PIP joint 120, as shown in the nonlimiting depicted embodiment), and compression/distraction actuators (depicted as locking nuts 80) that are lockable to prevent translation of one or more of the clamped pins along an axis defined by the stabilization rod 52 of the rod assembly 50. Referring to FIG. 1, as shown in the depicted embodiment, the fixator/distractor device 10 includes two modules that include at least one clamp 70 engaged with a bone pin 60, the modules including a distraction module 20 which is engaged on the distal bone of the joint (the distal phalanx 110 of the PIP joint 120, as shown in the nonlimiting depicted embodiment), and a stabilization module 30 which is engaged on the proximal bone of the joint (the proximal phalanx 130 of the PIP joint 120, as shown in the nonlimiting depicted embodiment). It will be appreciated that while the fixator/distractor device 10 is shown in the drawings, for example, FIG. 1, in association with a hand joint, the fixator/distractor device 10 may be used in the context of other anatomical joints and is neither limited to use in hands nor in joints of humans.

Figure 3:
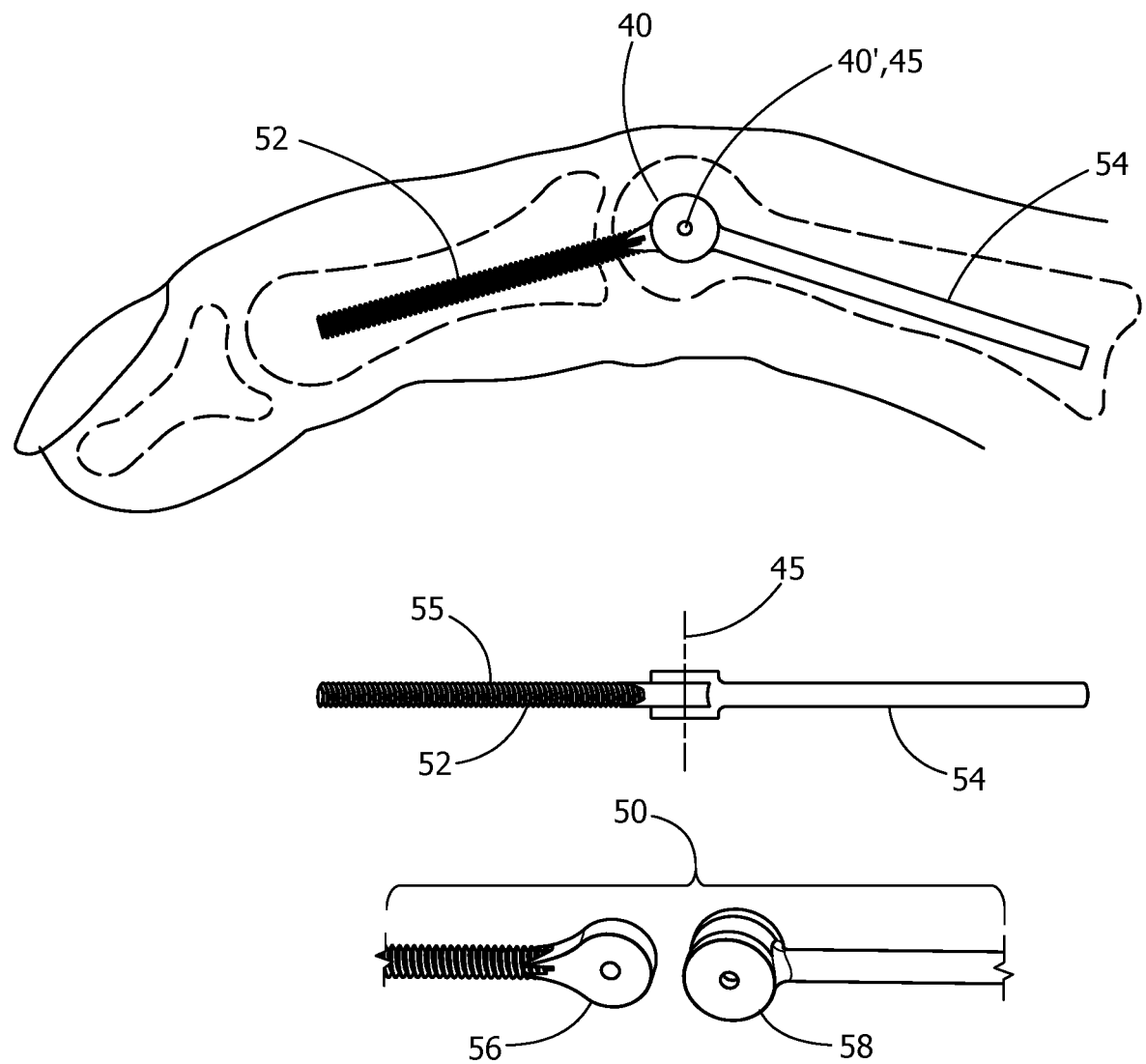
FIG. 3 shows in the top panel a side view of a digit of a human hand with the rod assembly components of the medical fixation device as shown in FIG. 1 depicted in reference to the finger bones to which the device is attached, and in the middle panel a top view of the engagement between the rod assembly components of the exemplified medical fixation device, and in the lower panel a side perspective view of the disengaged/uncoupled rod assembly components of the exemplified medical fixation device.

Generally, in use, the fixator/distractor device 10 is affixed to the bones adjacent proximal and distal to the joint, at least one distraction rod 52 being affixed with one or more pins 60 and clamps 70 to a bone that is proximal to the joint, and at least one and the stabilization rod 54 being affixed with one or more pins 60 and clamps 70 to a bone that is distal to the joint. Referring now to FIG. 3, the rod assembly 50 is formed via engagement features at each of the rod 52, 54 ends to form a pivot axis 45 that is aligned with the pivot axis of the joint as defined by the head of the proximal bone, which in the depicted embodiments is the proximal phalanx head 40. The rods 52, 54 are rigid to maintain stability of the pins 60 within the bones, and the pivot axis 45 is positioned proximate to the natural pivot axis of the joint to allow flexion around the joint via rotation of the distraction rod 52 relative to the stabilization rod 54 around the pivot axis 45, which rotation may be free or constrained by rotational stops.

Figure 2:
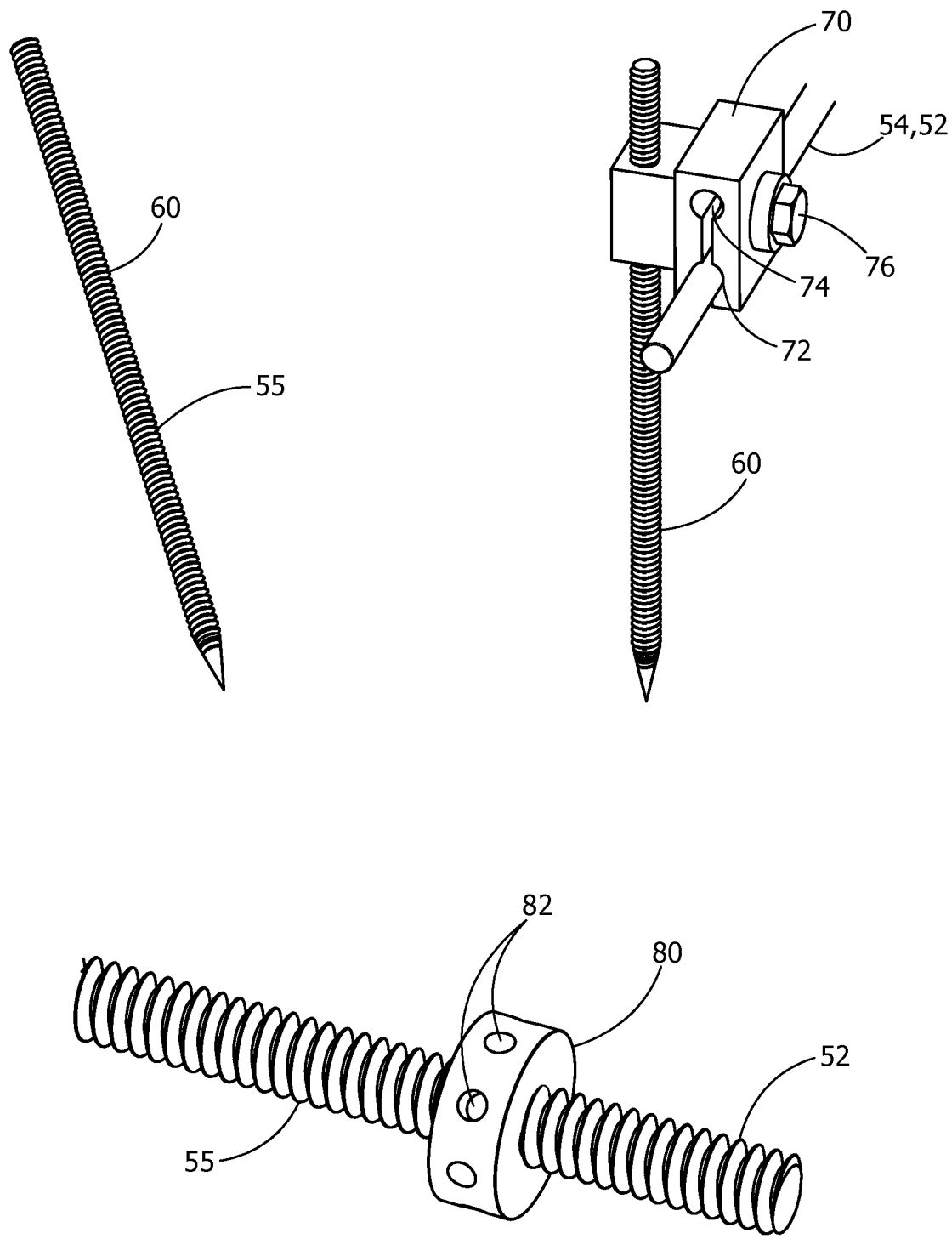
FIG. 2 shows detail of components of the medical fixation device as shown in FIG. 1, which include in the upper left a representative bone pin (wire), and in the upper right an assembly of a bone pin, clamp and seated rod, and on the bottom a threaded rod and locking nut.

Referring again to FIG. 1, as depicted, the fixator/distractor device 10 includes a pair of pins 60 that are inserted into the proximal bone and a pair of pins 60 that are inserted into the distal bone, the pins 60 all being inserted into the bone generally parallel to each other and to the pivot axis 45 of the joint when the digit is extended. Referring now to FIG. 2, as shown in the upper right panel, each pin 60 is fixed to a clamp 70. The clamp 70 is adapted with at least one rod retainer 72 which forms a seat for receiving and permitting adjustment of position of the clamp 70 along the axis of a seated rod 52, 54. When the clamp 70 is not locked to the seated rod 52, 54, the rod may slide or float within the rod retainer 72. Upon locking of the clamp 70, which may be achieved by actuation of a fastener, depicted in the drawings as a nut and bolt locking assembly 76, the seated rod 52, 54 is locked within the clamp 70 to preclude sliding motion along the rod axis. In some embodiments, the clamp 70 may include a slot that joins the rod retainer 72 with a flexion relief 74 to allow flexion of the clamp 70 for purposes of rod seating within the rod retainer 72.

Referring again to FIG. 1, the fixator/distractor device 10 includes distraction and stabilization modules 20, 30. In the depicted embodiment, these modules 20, 30 include a pair of clamp 70 and pin 60 assemblies. In other embodiments, there may be only one clamp 70 and pin 60 assembly in a module, or there may be more than two clamp 70 and pin 60 assemblies in a module. In use, upon fixation of all pins 60 with bone, the distraction module 20 comprising one or more clamp 70 and pin 60 assemblies is slidably translated along the distraction rod 52 until suitable distraction of the distal bone is achieved, whereupon the distraction module 20 is locked in place to preclude further translation by the actuation of each clamp 70 locking assembly 76. In certain embodiments, one or more compression/distraction actuators, locking nuts 80 may be used to enhance locked retention of the distraction module 20.

Referring again to FIG. 1, the distraction rod 52 that is affixed to the distal bone via the distraction module 20 includes the compression/distraction actuators, locking nuts 80, which operate in some embodiments to facilitate distally or proximally directed translation of the distal bone relative to the joint and the proximal bone when the clamp 70 is not locked, and to enhance retention of the distraction module 20 when the clamp 70 is locked. The stabilization rod 54 that is affixed to the proximal bone via the stabilization module 30 remains fixed relative to the joint and the distal bone.

Referring now to FIG. 2 and FIG. 3, in the depicted embodiment, the stabilization rod 54 is smooth and the distraction rod 52 is threaded 55 for engagement with corresponding threads on the compression/distraction actuators, locking nuts 80 to enable locking of the distraction module 20 to prevent its translation along the axis of the distraction rod 52. Further detail of the compression/distraction actuators, locking nuts 80 is shown in the lower panel of FIG. 2, which shows a locking nut 80 threadedly engaged with the threads 55 on the distraction rod 52. As depicted, the locking nut 80, includes driver receivers 82 which are engageable with a suitable tool to drive rotation of the nut 80 around the rod 54 and into contact with a clamp for locking the position of the clamp 70 along the rod axis.

It will be appreciated that in some embodiments, the distraction rod 52 may comprise threads 55 along all or only a portion of its surface insofar as the depicted mechanism does not rely on the threads 55 for engagement with the clamp 70. Thus, the distraction rod 52 may be smooth along a portion of its surface. And it will be further appreciated that in some embodiments, the distraction rod 52 may have other surface features suited to engagement of the clamp and other structures wherein motion of the distraction module 20 and any locking element is achieved by a means other than as described herein, for example a ratchet or worm drive/gear mechanism.

Referring now to FIG. 3, as shown in the bottom panel, the rod assembly 50 includes a pivot head 56 and a pivot clevis 58, which interengage to form a pivot joint that, in use when applied to the anatomy, is aligned with the head of the proximal bone to establish the pivot axis for the rod assembly 50. It will be appreciated that though the depicted embodiment includes the pivot head 56 on the distraction rod 52, and the pivot clevis 58 on the stabilization rod 54, the orientation of these components may be switched. Moreover, other structures may be employed to engage the rods 52, 54 and form the pivot axis 45 and thus the devices hereof are not limited to employment of these specific structures.

In use, when the rod assembly 50 is engaged with each of the distraction and stabilization modules, 20, 30 which are engaged via their respective pins 60 with the proximal and distal bones, the engaged monoplanar fixator/distractor device 10 enables controlled natural motion of the joint around the pivot axis while retaining selected and fixed distraction between the proximal and distal bones. The pivot axis also includes apertures in each of the pivot head 56 on the distraction rod 52, and the pivot clevis 58 on the stabilization rod 54 to allow for passage of a reference pin or wire (for example a Kirchner or K wire) into the bone head, as depicted in the drawings, the proximal phalanx head 40, to establish the initial position of the fixator/distractor device 10 relative to the natural pivot axis of the joint at the proximal phalanx head 40. Upon establishing the axis for the system, the various components are assembled and upon removal of the reference pin, the apertures in each of the pivot head 56 on the distraction rod 52, and the pivot clevis 58 on the stabilization rod 54 may receive a locking pin or other fastener to secure the engagement ends of the rods 52, 54 together and to allow for pivotal action at the pivot axis 45.

While the exemplified device includes a distraction module translation system that includes a clamps that are slidable on the distraction rod and employ a threaded rod and locking nut, it should be appreciated that other means may be employed to achieve translation of the distraction module in order to adjust distraction of the distal bone, and locking of the position once the level of distraction is selected. Thus, in other embodiments, a mechanism such as a ratchet mechanism, or a worm drive/gear mechanism may be employed, it being appreciated that it is the translation of the distal bone along an axis defined by the rod frame that enables selection of distraction position, where the means of such translation is not limited to any particular mechanism from among those known generally in the mechanical arts.

The exemplified device beneficially provides stability due to the fixation of bones proximal and distal to fracture with two bicortical pins on each side of the joint. The exemplified device provides a hinged design based on joint axis, to allow more anatomic mobilization of affected joint while applied. The monoplanar design of the device components minimizes bulk to improve patient tolerance. And the device may be constructed with radiolucent components to allow optimal visualization of fracture dislocation under fluoroscopy so as to facilitate initial placement of the pins and adjustment of distraction.

As used herein, the singular forms "a," "an," and "the" are intended to include the plural forms as well, unless the context clearly indicates otherwise. Anatomical references as used herein are intended to have the standard meaning for such terms as understood in the medical community. For example, the application may include reference to the following terms: volar (the front, as opposed to the back); dorsal (the back or behind, as opposed to the front); inferior (below, as opposed to superior); superior (above, as opposed to inferior); lateral (toward the left or right side of the body, as opposed to toward the middle); medial (in or toward the middle or inside of the body, as opposed to away from toward the left or right); proximal (toward the body, as opposed to toward the ends, such as of the fingers and hands); and distal (away from the body, as opposed to towards the body).

Unless otherwise indicated, all numbers expressing quantities, properties, and so forth as used in the specification and claims are to be understood as being modified in all instances by the term "about." Accordingly, unless otherwise indicated, the numerical properties set forth in the specification and claims are approximations that may vary depending on the suitable properties desired in embodiments of the present invention. Notwithstanding that any numerical ranges and parameters setting forth the broad scope of the general inventive concepts are approximations, numerical values set forth in the specific examples are reported as precisely as possible. Any numerical values, however, inherently contain certain errors necessarily resulting from error found in their respective measurements.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts.

Those skilled in the art may readily adopt one or more of the inventive aspects, concepts or features into additional embodiments and uses within the scope of the general inventive concepts even if such embodiments are not expressly disclosed herein. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated. Further, while disclosed benefits, advantages, and solutions to problems have been described with reference to specific embodiments, these are not intended to be construed as essential or necessary to the invention.

The invention claimed is:

1. A device for stabilizing a bone joint comprising:
   a plurality of pins for insertion into bones adjacent an anatomical joint, and
   a planar assembly comprising:
      a plurality of clamps engageable with one or more of each of the plurality of pins;
      at least two rods, each rod having a rod axis and an engagement feature that is complementary with an engagement feature on at least one other rod, the at least two rods being joinable to form a releasable and adjustable pivot joint that defines a singular pivot axis that is transverse to the axis of each of the joined rods, the rods being constrained to move relative to one another only around the singular pivot axis, and
      an actuator attachable to at least one rod and engageable therewith for contacting at least one clamp, the actuator and the at least one rod each comprising complementary translation features to direct translation of one or more clamps along the rod axis,
   wherein each of the rods is engageable with one or more of the plurality of pins via one or more of the plurality of clamps to provide a monoplanar assembly wherein each of the plurality of pins are aligned in parallel with the singular pivot axis, and wherein at least a first pin of the plurality of pins is affixed to one rod via a clamp that is engaged with an actuator, whereby actuation of the actuator moves the first pins towards or away from the pivot joint.

2. A device for stabilizing a bone joint according to claim 1, comprising four pins, four clamps, two rods and one actuator, wherein two pins are fixedly clamped to a first rod, and two pins are releasably clamped to a second rod, the pins clamped to the second rod providing a distraction module that is in communication with the actuator to direct translation of the distraction module along the axis of the second rod so as to move the distraction module.

3. A device for stabilizing a bone joint according to claim 1, wherein one or more of the pins, clamps and rods is radiolucent.

4. A device for stabilizing a bone joint according to claim 2, wherein the first rod has a generally smooth surface and wherein the second rod comprises a thread along at least a portion of its surface, and wherein the actuator is a nut with a through hole that receives the threaded second rod and includes on the surface of the through hole a complementary thread to engage with the threaded second rod.

5. The device for stabilizing a bone joint according to claim 1, the device comprising two rods joined to provide the transverse pivot, and two engagement modules each comprising a bone pin engaged with a bone clamp, each of the two engagement modules engaged with one of each of the two rods, wherein one of the modules is movable along the rod to which it is engaged.

6. A joint distraction device, comprising:
   (i) a plurality of bone pins suitable for insertion into bone;
   (ii) a plurality of clamps, each clamp connectible to a rod and to at least one bone pin of the plurality of the plurality of bone pins; and
   (iii) a rod assembly comprising a pair of rods including a distraction rod and a stabilization rod, joinable at respective ends to form a releasable pivot joint that defines a singular pivot axis,
   wherein the plurality of bone pins and plurality of clamps are assembled to form two modules, each module including at least one clamp engaged with at least one bone pin, the modules including a distraction module connectable to and movable along the distraction rod, and a stabilization module connectable to the stabilization rod, to provide a monoplanar assembly wherein each of the plurality of pins are aligned in parallel with the singular pivot axis.

7. The joint distraction device according to claim 6, wherein the device is adjustable to enable controlled and lockable distraction when the each of the stabilization module and the distraction module is affixed to bones that are respectively proximal and distal to a joint by displacement of the distraction module either proximally or distally along the distraction rod.

8. The joint distraction device according to claim 6, wherein the device permits rotation within only a single degree of freedom of one or both rods around the singular pivot axis.

9. The joint distraction device according to claim 8, wherein the device is adapted to be lockable to prevent dynamic flexion and extension of the anatomy.

10. The joint distraction device according to claim 9, wherein restriction of motion may be complete using stops or other locks on the singular pivot axis.

11. The joint distraction device according to claim 9, wherein in some embodiments motion may be partially restricted with limits on the range of flexion/extension.

12. The joint distraction device according to claim 6, wherein the pins, rods and wires are formed of metal, selected from stainless steel, titanium and other suitable medical grade metals.

13. The joint distraction device according to claim 6, wherein the rods and clamps are formed primarily of radiolucent material.

14. The joint distraction device according to claim 13, wherein the radiolucent materials include tantalum or other type radiopaque markers to register position of the device radiographically when applied to the anatomy.

15. A method for providing distraction and anatomical motion to a fixated joint, the method comprising:
   (a) providing a joint distraction device comprising at least two bone engagement modules that each comprise at least one assembly comprising a bone pin connectible to a clamp, each clamp in turn connectible to a rod, the device further comprising two elongate rigid rods that are connectible at respective ends to one another to form a rod assembly that can be extended to form a substantially linear rigid assembly, each of the rods having a shared axis, the rod assembly including a constrained singular pivot axis at the joinder of the rod ends, the singular pivot axis being perpendicular to the rod shared axis, wherein at least one bone engagement module is connectible to one rod to form a stabilization portion and at least one bone engagement module is connectible to the other rod to form a distraction portion, and
   (b) applying the device to a side of an anatomical joint, the application including a first step that includes placement of a guide wire in a bone that is immediately proximal to the joint at a head of the bone that forms a native anatomic pivot axis of the joint, sliding the rod assembly on the guide wire by passage of the wire through an aperture at the singular pivot axis of the rod assembly, affixing a stabilization bone engagement module to the stabilization rod and passing the bone pin thereof into bone that is proximal to the joint, affixing a distraction bone engagement module to the distraction rod and passing the bone pin thereof into bone that is distal to the joint, each of the bone pins being aligned in parallel with the singular pivot axis adjusting the distance between the two bone engagement modules by translating the distraction module either proximally or distally to select a displacement position, locking the distraction module onto the distraction rod, and removing the guide wire and inserting a fastener that one of permits or limits rotation of one or both rods at the rod assembly singular pivot axis.

16. The method for providing distraction and anatomical motion to a fixated joint according to claim 15, wherein the pins, rods and wires are formed of metal, selected from stainless steel, titanium and other suitable medical grade metals.

17. The method for providing distraction and anatomical motion to a fixated joint according to claim 15, wherein the rods and clamps are formed primarily of radiolucent material.

18. The method for providing distraction and anatomical motion to a fixated joint according to claim 15, wherein the radiolucent materials include tantalum or other type radiopaque markers to register position of the device radiographically when applied to the anatomy.

19. A joint distraction device comprising:
at least two bone engagement modules that each comprise at least one assembly comprising at least one bone pin and a clamp, each clamp being connectible to the at least one bone pin and a rod, the device further comprising two elongate rigid rods that are connectible at respective ends to one another to form a rod assembly that can be extended to form a substantially linear rigid assembly, each of the rods having a shared axis, the rod assembly including a constrained singular pivot axis at the joinder of the rod ends, the axis being perpendicular to the rod shared axis,
wherein one or more of the rods may be moved off the shared axis by rotation of its end around the rod assembly singular pivot axis, and wherein at least one bone engagement module is connectible to one rod to form a stabilization portion and at least one bone engagement module is connectible to the other rod to form a distraction portion, wherein each of the bone pins of the bone engagement modules are aligned in parallel with the singular pivot axis, and wherein translation of the bone engagement module of the distraction portion along the rod axis provides for relative displacement between the two bone engagement modules.

20. The joint distraction device according to claim 19, wherein the device is adapted for fixation to respective proximal and distal bones at a joint axis between the bones with the singular pivot axis aligned with the joint axis, and wherein upon engagement therewith via insertion of the pins into the respective bones, a displacement of the bone engagement model fixed to the distal bone either distracts or compresses the joint between the bones, and wherein upon locking of the position of the bone engagement model fixed to the distal bone, the device fixates the joint and the singular pivot axis of the rod assembly permits constrained motion of the distal bone around the singular pivot axis.

\* \* \* \* \*